(12) United States Patent
Lehnhardt et al.

(10) Patent No.: US 11,266,418 B2
(45) Date of Patent: Mar. 8, 2022

(54) INTEGRATED MEDICAL DEVICE CONSTRAINING LUMEN

(71) Applicant: W. L. Gore & Associates, Inc., Newark, DE (US)

(72) Inventors: Eric C. Lehnhardt, Tempe, AZ (US); Martin J. Sector, Gilbert, AZ (US); Franklin C. Wetherell, Flagstaff, AZ (US); Karl R. Chung, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 15/670,494

(22) Filed: Aug. 7, 2017

(65) Prior Publication Data

US 2018/0036011 A1 Feb. 8, 2018

Related U.S. Application Data

(60) Provisional application No. 62/371,372, filed on Aug. 5, 2016.

(51) Int. Cl.
| | |
|---|---|
| *A61F 2/07* | (2013.01) |
| *A61F 2/95* | (2013.01) |
| *A61B 17/12* | (2006.01) |
| *A61F 2/966* | (2013.01) |
| *A61F 2/958* | (2013.01) |

(52) U.S. Cl.
CPC ......... *A61B 17/12118* (2013.01); *A61F 2/07* (2013.01); *A61F 2/958* (2013.01); *A61F 2/9662* (2020.05); *A61B 2017/1205* (2013.01); *A61F 2002/9511* (2013.01); *A61F 2210/0076* (2013.01); *A61F 2230/0034* (2013.01)

(58) Field of Classification Search
None
See application file for complete search history.

(56) References Cited

U.S. PATENT DOCUMENTS

| | | | |
|---|---|---|---|
| 6,168,618 B1 | 1/2001 | Frantzen | |
| 6,203,550 B1 | 3/2001 | Olson | |
| 6,520,986 B2 * | 2/2003 | Martin | ...................... A61F 2/07 623/1.13 |
| 6,733,521 B2 | 5/2004 | Chobotov et al. | |
| 6,761,733 B2 | 7/2004 | Chobotov | |
| 6,911,039 B2 | 6/2005 | Shiu | |
| 6,974,471 B2 | 12/2005 | Van Schie | |

(Continued)

FOREIGN PATENT DOCUMENTS

| | | |
|---|---|---|
| EP | 1474074 B1 | 4/2004 |
| EP | 1441668 B1 | 1/2008 |

(Continued)

OTHER PUBLICATIONS

International Search Report and Written Opinion of PCT/US2017/045722, dated Oct. 10, 2017, 11 pages.

*Primary Examiner* — Leslie Lopez

(57) ABSTRACT

Various aspects of the present disclosure are directed toward apparatuses, systems, and methods that include an implantable medical device and a constraining line conduit arranged around a circumference of the implantable medical device. The apparatuses, systems, and methods may also include a constraining line arranged through the constraining line conduit.

17 Claims, 6 Drawing Sheets

(56) References Cited

U.S. PATENT DOCUMENTS

| | | |
|---|---|---|
| 7,081,132 B2 | 7/2006 | Cook |
| 7,147,661 B2 | 12/2006 | Chobotov |
| 7,655,034 B2 | 2/2010 | Mitchell et al. |
| 7,837,724 B2 | 11/2010 | Keeble |
| 7,938,851 B2 | 5/2011 | Olson |
| 7,976,575 B2 | 7/2011 | Hartley |
| 8,167,927 B2 | 5/2012 | Chobotov |
| 8,241,346 B2 | 8/2012 | Chobotov |
| 8,257,431 B2 | 9/2012 | Henderson |
| 8,262,671 B2 | 9/2012 | Osypka |
| 8,328,861 B2 | 12/2012 | Martin |
| 8,361,135 B2 | 1/2013 | Dittman |
| 8,480,725 B2 | 7/2013 | Rasmussen |
| 8,808,355 B2 | 8/2014 | Barrand |
| 8,968,384 B2 | 3/2015 | Pearson |
| 9,060,895 B2 | 6/2015 | Hartley |
| 9,125,764 B2 | 9/2015 | Shaw |
| 9,132,025 B2 | 9/2015 | Aristizabal |
| 9,254,204 B2 | 2/2016 | Roeder |
| 9,308,349 B2 | 4/2016 | Rezac |
| 9,358,142 B2 | 6/2016 | Johnson |
| 9,498,361 B2 | 11/2016 | Roeder |
| 9,585,743 B2 | 3/2017 | Cartledge |
| 9,585,774 B2 | 3/2017 | Aristizabal |
| 9,681,968 B2 | 6/2017 | Goetz |
| 9,700,701 B2 | 7/2017 | Benjamin |
| 9,782,284 B2 | 10/2017 | Hartley |
| 9,937,070 B2 | 4/2018 | Skelton |
| 2002/0151953 A1* | 10/2002 | Chobotov ............... A61F 2/954 623/1.11 |
| 2007/0225797 A1 | 9/2007 | Krivoruhko |
| 2008/0269866 A1 | 10/2008 | Hamer |
| 2009/0132026 A1 | 5/2009 | Martin |
| 2010/0114290 A1 | 5/2010 | Rasmussen et al. |
| 2010/0114291 A1 | 5/2010 | Kolbel |
| 2011/0276062 A1 | 11/2011 | Bolduc |
| 2013/0123896 A1 | 5/2013 | Bloss et al. |
| 2014/0148895 A1 | 5/2014 | King |
| 2014/0180385 A1 | 6/2014 | Majercak et al. |
| 2014/0194968 A1 | 7/2014 | Zukowski |
| 2016/0184118 A1 | 6/2016 | Faber |
| 2016/0193032 A1 | 7/2016 | Dake |
| 2017/0172724 A1 | 6/2017 | Cartledge |
| 2017/0281382 A1 | 10/2017 | Lostetter |

FOREIGN PATENT DOCUMENTS

| | | |
|---|---|---|
| EP | 1915113 B1 | 3/2010 |
| EP | 1358903 B1 | 2/2011 |
| EP | 2745812 A1 | 6/2014 |
| EP | 2749251 B1 | 7/2016 |
| EP | 2956198 B1 | 11/2017 |
| GB | 2464978 A | 5/2010 |
| JP | 2012-507345 A | 3/2012 |
| JP | 2014-121612 A | 7/2014 |
| JP | 2014-533189 A | 12/2014 |
| WO | WO-1998011847 A1 | 3/1998 |
| WO | WO-2003053495 A2 | 7/2003 |
| WO | WO-2009148607 A1 | 12/2009 |
| WO | 2010/062362 A1 | 6/2010 |
| WO | 2013/074266 A1 | 5/2013 |

* cited by examiner

INTEGRATED MEDICAL DEVICE CONSTRAINING LUMEN

CROSS-REFERENCE TO RELATED APPLICATION

This application claims priority to Provisional Application No. 62/371,372, filed Aug. 5, 2016, which is herein incorporated by reference in its entirety.

FIELD

The present disclosure relates generally to implantable medical devices. More specifically, the present disclosure relates to apparatuses, systems, and methods of constraining implantable medicals.

BACKGROUND

Implantable medical devices are frequently used to treat the anatomy of patients. Such devices can be permanently or semi-permanently implanted in the anatomy to provide treatment to the patient. Frequently, these devices, including stents, grafts, stent-grafts, filters, valves, occluders, markers, mapping devices, therapeutic agent delivery devices, prostheses, pumps, bandages, and other endoluminal and implantable devices, are inserted into the body at an insertion point and deployed to a treatment area using a catheter.

The implantable medical devices may be configured in a constrained configuration in order to direct the implantable medical device through the vasculature of the patient to the desired treatment area. Once the implantable device reaches the treatment area, the device is properly oriented and deployed, from the constrained configuration, to provide treatment. Such orientation and deployment is actuated by a physician using elements outside of the body of the patient.

SUMMARY

Various aspects of the present disclosure are directed toward apparatuses, systems, and methods that include an implantable medical device and a constraining line conduit arranged around a circumference of the implantable medical device. The apparatuses, systems, and methods may also include a constraining line arranged through the constraining line conduit. The constraining line may be configured to constrain at least a portion of the implantable medical device in response to tensioning of the constraining line While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure.

Figure 1:
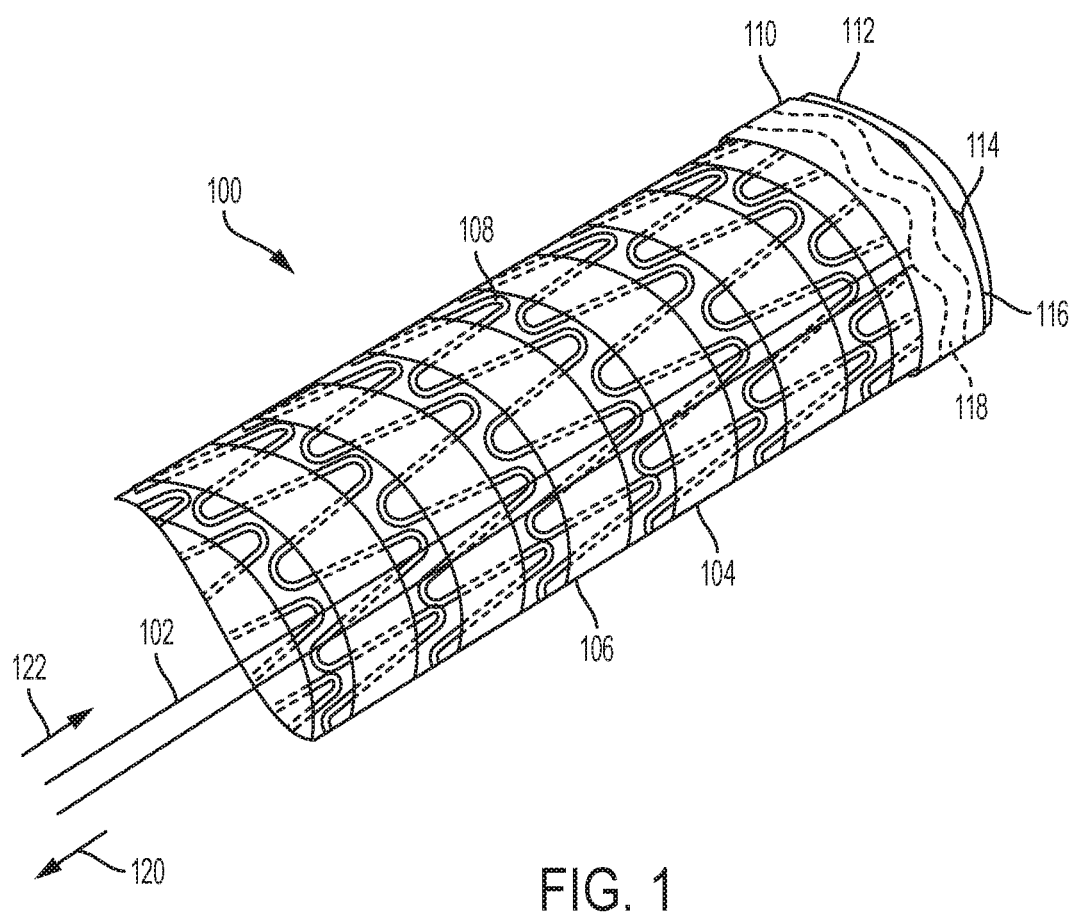
FIG. 1 is a partial perspective view of an implantable medical device and constraining line in accordance with various aspects of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

DETAILED DESCRIPTION

FIG. 1 is a partial perspective view of an implantable medical device 100 and constraining line 102 in accordance with various aspects of the present disclosure. The implantable medical device 100 may include a graft component 104 and a stent component 106 arranged along an exterior surface of the graft component 104. The stent component 106 may include a stent pattern 108 having straight segments 110 and apices 112. In certain instances, the constraining line 102 can be arranged over the alternating straight segments 110 and/or alternating apices 112 around the circumference of implantable medical device 100 at the proximal end and perpendicular to a longitudinal axis of the implantable medical device 100. In other instances, the constraining line 102 can be arranged over the alternating straight segments 110 and/or alternating apices 112 at an angle relative to the longitudinal axis of the implantable medical device 100. In order to position the constraining line 102 in a desired positon, the implantable medical device 100 may further include a constraining line conduit 118 as is discussed in further detail with respect to FIGS. 2-3 and 5. The constraining line conduit 118 provides a pathway through which the constraining line 102 may be arranged, as opposed to threading the constraining line 102 through the alternating straight segments 110 and/or alternating apices 112 of the stent pattern 108 and/or through the graft component 104. The constraining line conduit 118 may mitigate against the constraining line 102 catching on the stent pattern 108 and/or through the graft component 104 and mitigate against adverse interaction with other components (e.g. guidewires, catheters, balloons) that may be introduced during the implantation and delivery of the implantable medical device 100.

In certain instances, the implantable medical device 100 is inserted into the vasculature of the patient in a collapsed configuration and directed to a treatment area of the patient. Upon reaching the treatment area, the implantable medical device 100 is expanded to deployed configuration. The constraining line 102 may constrain or assist in constraining the implantable medical device 100 in the collapsed configuration.

The constraining line 102 may include or form a loop 114. The constraining line 102 may extend through the loop 114 to form a slip knot and travel to a distal end 116 of the implantable medical device 100 to the outside of the body of the patient. In certain instances, the loop 114 can comprise an end loop, such that when constraining line 102 passes through loop 114, it forms a slip knot. In such instances, the constraining line 102 comprises a line or wire looped into the loop 114, thereby creating two segments. Both segments pass through loop 114 to form the slip knot, and then travel back along the length of the delivery device and outside of the patient. The resulting slip knot can extend about and releasably restrain the proximal end of the implantable medical device 100 axially and/or radially.

The constraining line 102 may include two segments (as shown). In order to tension the constraining line 102 and constrain the implantable medical device 100 axially and/or radially, an operator can release one of the segments of constraining line 102 and provide tension to the other segment in a first direction 120. Pulling the constraining line 102 in the first direction 120 may close the loop 114, and constrain the implantable medical device 100 axially and/or radially. In order to deploy the implantable medical device 100 from the constrained configuration, the tension applied in the first direction 120 may be released. Further, the constraining line 102 may be uncoupled or removed from the implantable medical device 100. By pulling the constraining line 102 in a second direction 122, the released segment can travel in the second direction 122 and pass through the constraining line conduit 118, and travel back to the operator. In addition, one or more segments of the constraining line 102 can be removably coupled to a catheter handle. In such embodiments, the catheter handle can comprise a release button that, when activated, releases one of the segments of the constraining line 102 for removal thereof.

Figure 2:
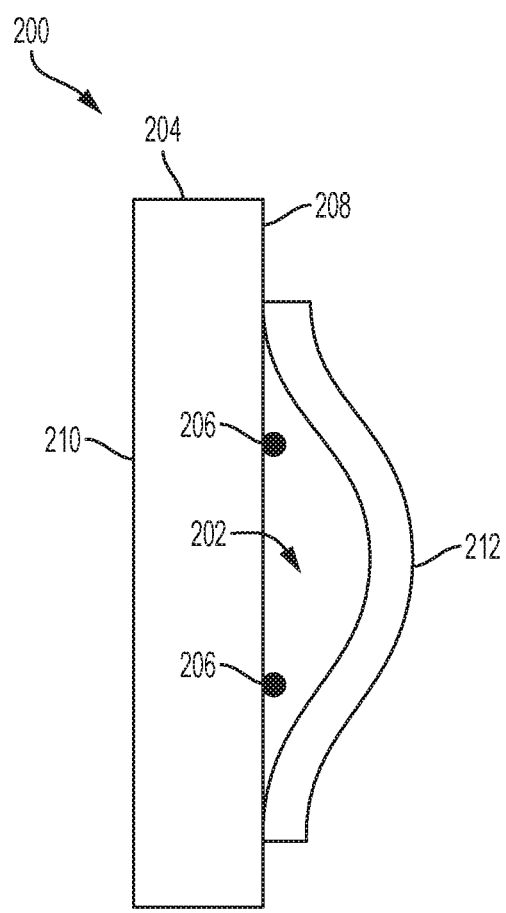
FIG. 2 is a cross-sectional view of an implantable medical device and constraining line conduit in accordance with various aspects of the present disclosure.

FIG. 2 is a cross-sectional view of an implantable medical device 200 and constraining line conduit 202 in accordance with various aspects of the present disclosure. The implantable medical device 200 may include a graft portion 204 and a stent portion 206. The stent portion 206 may be arranged on an exterior surface 208 of the graft portion 204. The graft portion 204 also includes an interior surface 210, which forms an internal lumen of the implantable medical device 200. The constraining line conduit 202 may be arranged around a circumference of the implantable medical device 200 (e.g., as shown in FIG. 1) on the exterior surface 208 of the graft portion 204 with the stent portion 206 being arranged between the exterior surface 208 of the graft portion 204 and the constraining line conduit 202. The constraining line conduit 202 may include a discontinuity or gap at some point around the circumference of the implantable medical device 200. The discontinuity or gap in the constraining line conduit 202 may allow for a constraining line to be arranged through the constraining line conduit 202.

The constraining line conduit 202 may be formed by a graft portion 212 that is attached to the exterior surface 208 of the graft portion 204. In addition, the constraining line conduit 202 may include a first boundary and a second boundary. As shown in FIG. 2, the first boundary of the constraining line conduit 202 is the exterior surface 208 of the graft portion 204, and the second boundary is formed by the graft portion 212. As a result, the constraining line conduit 202 may provide a pathway through which a constraining line (not shown) may be arranged. The constraining line may constrain the implantable medical device 200 axially and/or radially in response to tension applied thereto.

FIG. 3A is a cross-sectional view of the implantable medical device 300 and constraining line conduit 302. The implantable medical device 300 may include a graft portion 304 and a stent portion 306. The stent portion 306 may be arranged on an exterior surface of the graft portion 304. The constraining line conduit 302 may be formed by a first graft portion 308 that is attached to the exterior surface of the graft portion 304. The first graft portion 308 may be bonded on the exterior surface of the graft portion 304. As shown in FIG. 3A, a wire 310 may be arranged between the exterior surface of the graft portion 304 and the first graft portion 308. The wire 310 may provide an obstruction during bonding of the first graft portion 308 to the exterior surface of the graft portion 304 such that end portions of the first graft portion 308 is bonded to the exterior surface of the graft portion 304.

After the first graft portion 308 is bonded to the exterior surface of the graft portion 304, the wire 310 may be removed. FIG. 3B is a cross-sectional view of the implantable medical device 300 and the constraining line conduit 302, as shown in FIG. 3A, that results from the wire 310 providing an obstruction to bond the end portions of the first graft portion 308 is bonded to the exterior surface of the graft portion 304. As shown in FIG. 3B, the wire 310 leaves behind a passage of the constraining line conduit 302 through which a constraining line 312 may be arranged. As a result, the constraining line conduit 302 may include a first boundary and a second boundary. As shown in FIG. 3B, the first boundary of the constraining line conduit 302 is the exterior surface of the graft portion 304, and the second boundary is formed by the first graft portion 308.

In certain instances, a second graft portion 314 may be arranged over the stent 306 within the bounds of the first graft portion 308. The second graft portion 314 may be bonded to the exterior surface of the graft portion similar to manner in which the first graft portion 308 is bonded to the exterior surface of the graft portion (e.g., an FEP adhesive). FIG. 3C is a cross-sectional view of the implantable medical device 300, the constraining line conduit 302, and the constraining line 312, as shown in FIGS. 3A-B, with second (additional) graft portion 314 in accordance with various aspects of the present disclosure. As a result, the second graft portion 314 may form the first boundary of the constraining line conduit 302, with the first graft portion 308 forming the second boundary. The constraining line conduit 302 may include a discontinuity or gap at some point around the circumference of the implantable medical device 300. The discontinuity or gap in the constraining line conduit 302 may allow for the constraining line 312 to be arranged through the constraining line conduit 302. More specifically, the circumference of the implantable medical device 300 may be between 25 mm and 50 mm. The discontinuity or gap in the constraining line conduit 302 may be between 0.5 mm and 3 mm. The remaining portions of the constraining line conduit 302 are continuous about the circumference of the implantable medical device 300.

The constraining line 312 may constrain the implantable medical device 300 axially and/or radially in response to tension applied thereto. In addition, the implantable medical device 300 may be constrained and unconstrained using the constraining line 312 between a constrained configuration (e.g., for delivery of the implantable medical device 300) and a deployed configuration (e.g., an operative state at a target therapy region). The implantable device 300 may be constrained and unconstrained multiple times to allow for repositioning of the implantable device 300 at the therapy location if the positioning is not desirable.

FIG. 4A is a cross-sectional view of an implantable medical device 400 and a constraining line conduit 402 in accordance with various aspects of the present disclosure. The implantable medical device 400 may include a graft portion 404 and a stent portion 406 (arranged on an exterior surface of the graft portion 404). The constraining line conduit 402 may be formed from a hollow fiber 410. The hollow fiber 410 may be attached to the exterior surface of the graft portion 404 by way of a graft layer 408. The graft layer 408 is attached to the exterior surface of the graft portion 404 around the hollow fiber 410. The graft layer 408 may also be attached to the hollow fiber 410. The hollow fiber 410 forms boundaries of the constraining line conduit 402. The graft layer 408 may be attached to the graft portion 404 and/or the hollow fiber 410 using an adhesive or the graft layer 408 may include a material layer (such as FEP) that acts as adhesive after heating and bond to the graft portion 404 and/or the hollow fiber 410.

The hollow fiber 410 may include discontinuity or gap to allow for a constraining line 414 (shown in FIG. 4C) to be arranged through the hollow fiber 410. More specifically, the circumference of the implantable medical device 400 may be between 25 mm and 50 mm. The discontinuity or gap in the hollow fiber 410 may be between 0.5 mm and 3 mm. The remaining portions of the hollow fiber 410 and the constraining line conduit 402 are continuous about the circumference of the implantable medical device 400.

As shown in FIG. 4B, a wire 412 may be used to form the constraining line conduit 402, as shown in FIG. 4A. The wire 412, which may be a Nitinol or stainless steel wire, may be arranged through the hollow fiber 410. The wire 412 may assist in threading a constraining line 414 through the hollow fiber 410 as shown in FIG. 4C. As shown in FIG. 4C, the constraining line 414 is arranged through the hollow fiber 410 in place of the wire 412.

The constraining line 414 may constrain the implantable medical device 400 to a constrained configuration (e.g., between approximately between 5% and 20% of an unconstrained diameter of the implantable medical device 400) in response to tension applied to the constraining line 414. In addition, the implantable medical device 400 may be constrained and unconstrained multiple times to allow for repositioning of the implantable device 400 at the therapy location if the positioning is not desirable. The constrained configuration of the implantable device 400 may be used for delivery of the implantable medical device 400 and a deployed configuration may be an operative state at a target therapy region). In addition, the implantable device 400 may be partially constrained between the constrained configuration and the deployed configuration based on the amount of tension applied to the constraining line 414. The implantable device 400 may be imaged during an implantation procedure to determine if the implantable medical device 400 is implanted at the desired location and with the desired position. As such, an operator may view the amount the implantable medical device 400 is constrained via the constraining line 414 and adjust the amount of tension applied to the constraining line 414.

Figure 3:
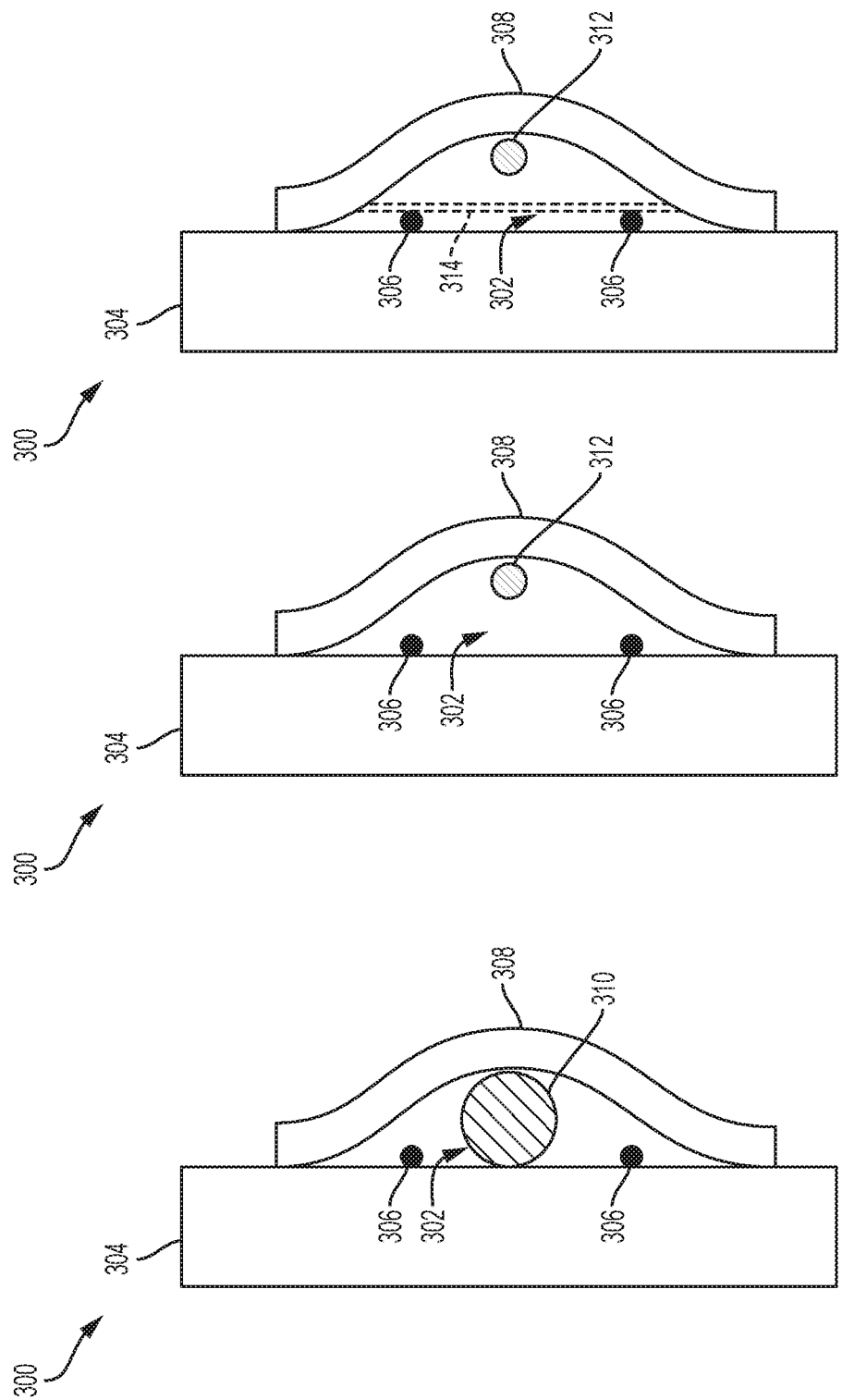
FIG. 3A is a cross-sectional view of the implantable medical device and constraining line conduit with a wire that may be used to form the constraining line conduit in accordance with various aspects of the present disclosure.
FIG. 3B is a cross-sectional view of the implantable medical device and constraining line conduit, as shown in FIG. 3A, with a constraining line arranged through the constraining line conduit in accordance with various aspects of the present disclosure.
FIG. 3C is a cross-sectional view of the implantable medical device and constraining line conduit, and the constraining line, as shown in FIGS. 3A-B, with an optional additional graft layer in accordance with various aspects of the present disclosure.
Figure 4:
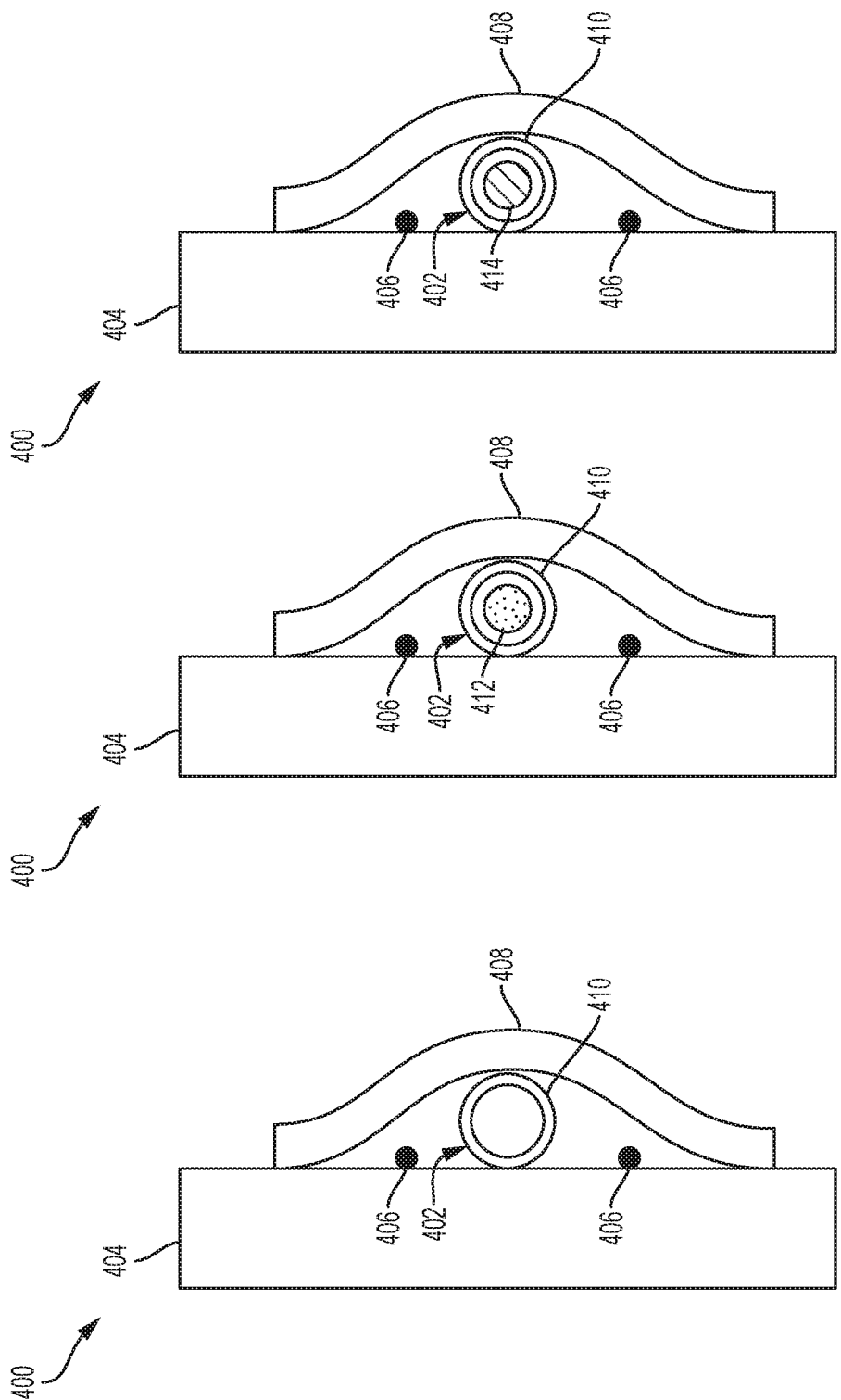
FIG. 4A is a cross-sectional view of an implantable medical device and a constraining line conduit in accordance with various aspects of the present disclosure.
FIG. 4B is a cross-sectional view of the implantable medical device and the constraining line conduit, as shown in FIG. 4A, with a wire arranged through the constraining line conduit in accordance with various aspects of the present disclosure.
FIG. 4C is a cross-sectional view of the implantable medical device and the constraining line conduit, as shown in FIGS. 4A-B, with a constraining line arranged through the constraining line conduit in accordance with various aspects of the present disclosure.

The illustrative components shown in FIGS. 2-4 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 2-4 may be, in embodiments, integrated with various other components depicted therein (and/or components not illustrated), all of which are considered to be within the ambit of the disclosed subject matter. More specifically, the constraining lines discussed with reference to FIGS. 2-4 may include similar structural aspects and capabilities as the constraining lines discussed with reference to FIGS. 1, 5, and 6.

Figure 5:
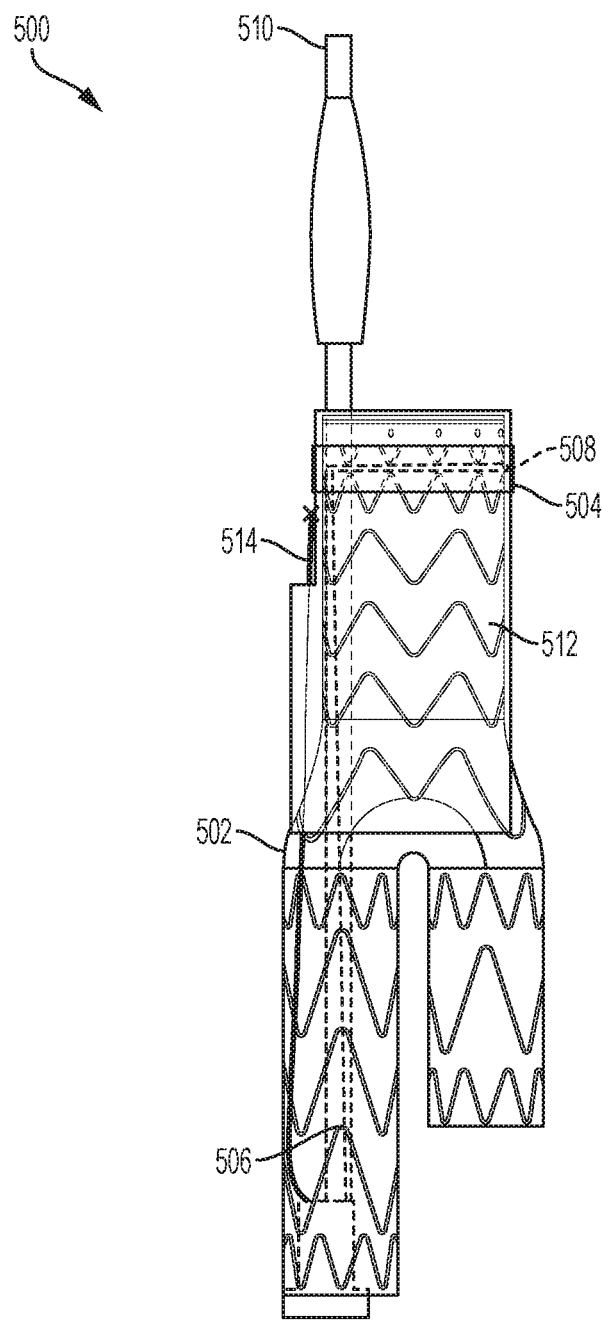
FIG. 5 is an illustration of a catheter arrangement that includes an implantable medical device, a constraining line conduit, and a constraining line arranged through the constraining line conduit in accordance with various aspects of the present disclosure.

FIG. 5 is an illustration of a catheter arrangement 500 that includes an implantable medical device 502, a constraining line conduit 504, and a constraining line 506 arranged through the constraining line conduit 504 in accordance with various aspects of the present disclosure. The catheter arrangement 500 may include a catheter shaft 510 with the implantable medical device 502 positioned at a distal end thereof. The implantable medical device 502 may be removably coupled to catheter shaft 510 by the constraining line 506. In addition, the implantable medical device 502 may be concentrically surrounded by at least one constraining sleeve, such as sleeve 512.

The constraining line 506 may constrain the implantable medical device 502 to a constrained configuration (e.g., between approximately between 5% and 20% of an unconstrained diameter of the implantable medical device 502) in response to tension applied to the constraining line 506. The entirety of the implantable medical device 502 may be constrained toward the catheter shaft 510 in response to tension applied to the constraining line 506 due to the arrangement of the constraining line 506 along the catheter shaft 510 for the length of the implantable medical device 502. In addition, the constraining line 506 may be arranged such that only a portion of the implantable medical device 400 is constrained in response to tension applied to the constraining line 506.

The implantable medical device 502 may be constrained and unconstrained multiple times to allow for repositioning of the implantable medical device 502 at the therapy location if the positioning is not desirable. The constrained configuration of the implantable medical device 502 may be used for delivery of the implantable medical device 502 and a deployed configuration may be an operative state at a target therapy region). In addition, the implantable medical device 502 may be partially constrained between the constrained configuration and the deployed configuration based on the amount of tension applied to the constraining line 506. The implantable medical device 502 may be imaged during an implantation procedure to determine if the implantable medical device 502 is implanted at the desired location and with the desired position. As such, an operator may view the amount the implantable medical device 502 is constrained via the constraining line 506 and adjust the amount of tension applied to the constraining line 506.

The constraining line conduit 504 may mitigate against the constraining line 506 catching on aspects of the implantable medical device 502 (e.g., stent pattern) by providing a pathway through which the constraining line 506 may be arranged. In the absence of the constraining line conduit 504, the constraining line 506 may have been weaved through the implantable medical device 502 (e.g., through the stent pattern or graft component). Weaving the constraining line 506 in this manner may increase the amount of force or tension needed to apply to the constraining line 506 in constraining the implantable medical device 502 toward the catheter shaft 510. In addition, the constraining line conduit 504 mitigates against adverse interaction with other components of the catheter arrangement 500 such as the catheter shaft 510 or a guidewire 514.

Figure 6:
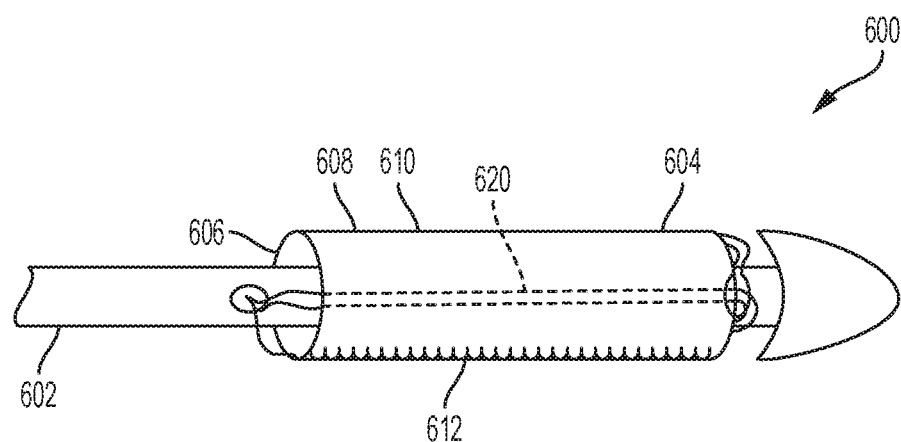
FIG. 6 illustrates a perspective view of a catheter assembly and implantable medical device in accordance with the present disclosure.

FIG. 6 illustrates a perspective view of a catheter assembly 600 and implantable medical device 604 in accordance with the present disclosure. The catheter assembly 600 may include a catheter shaft 602 with the implantable medical device 604 is positioned at a distal end of and removably coupled to catheter shaft 602 by a constraining line 620. The implantable medical device 604 may be concentrically surrounded by at least one constraining sleeve, such as sleeve 610.

In certain instances, the implantable medical device 604 is inserted into the vasculature of the patient in a collapsed configuration, wherein implantable medical device 604 is surrounded by sleeve 610 and held in a desired position relative to catheter shaft 602 by the constraining line 620. The implantable medical device 604 is then directed to a treatment area of the patient. Upon reaching the treatment area, the implantable medical device 604 is deployed. In certain instances, deployment of the implantable medical device 604 may include removing the sleeve 610 and removing the constraining line 620 from implantable medical device 604. In certain instances, the implantable medical device 604 is collapsed and/or compressed and positioned at the distal end of catheter shaft 602. The Implantable medical device 604 can then be navigated through the body of the patient to the treatment area.

In various embodiments, the implantable medical device 604 can comprise a radially collapsed configuration suitable for delivery to the treatment area of the vasculature of a patient. The Implantable medical device 604 can be constrained in a radially collapsed configuration and mounted onto the catheter shaft 602. The diameter of the implantable medical device 604 in the collapsed configuration is small enough for the implant to be delivered through the vasculature to the treatment area. In various embodiments, the diameter of the collapsed configuration is small enough to minimize the crossing profile of the catheter assembly 600 and minimize tissue damage to the patient. In the collapsed configuration, the implantable medical device 604 can be guided by the catheter shaft 602 through the vasculature. Once the implantable medical device 604 is in position in the treatment area of the vasculature, the implantable medical device 604 can be expanded to a radially expanded configuration.

In certain instances, the implantable medical device 604 can comprise a radially expanded configuration suitable for implanting the device in the treatment area of a patient's vasculature. In the expanded configuration, the diameter of the implantable medical device 604 can be approximately the same as the vessel to be repaired. In other instances, the diameter of implantable medical device 604 in the expanded configuration can be slightly larger than the vessel to be treated to provide a traction fit within the vessel.

In certain instances, the implantable medical device 604 can comprise a self-expandable device, such as a self-expandable stent-graft. Such devices dilate from a radially collapsed configuration to a radially expanded configuration when unrestrained. In certain instances, the implantable medical device 604 can comprise a device that is expanded with the assistance of a secondary device such as, for example, a balloon. The catheter assembly 600 may carry a plurality of implantable medical devices 604. The use of a catheter assembly 600 with any number of implantable medical devices is within the scope of the present disclosure.

Various medical devices in accordance with the disclosure comprise a sleeve or multiple sleeves. The sleeve or sleeves can constrain an implantable medical device in a collapsed configuration for endoluminal delivery of the implant to a treatment portion of the vasculature of a patient. For example, as illustrated in FIG. 6, the catheter assembly 600 includes the sleeve 610. The sleeve 610 may assist the constraining line 620 in constraining the implantable medical device 604 to a reduced diameter.

After delivery of the implantable medical device to the treatment portion of the vasculature of the patient, the sleeve or sleeves can be unconstrained in order to allow the implantable medical device to expand to its functional diameter and achieve the desired therapeutic outcome. In various instances, the sleeve or sleeves can remain implanted while not interfering with the implantable medical device. In other instances, the sleeve or sleeves can be removed from the body of the patient after successful deployment of the implantable medical device.

In various instances, the sleeve 610 may be formed from a sheet of one or more materials wrapped or folded about the implantable medical device. While the illustrative aspects herein are described as including one or more tubular sleeves, sleeves of any non-tubular shape that corresponds to an underlying implantable medical device or that are otherwise appropriately shaped for a given application are also within the scope of the present disclosure.

In various instances, when the implantable medical device 604 is in position within the vasculature, coupling member 612 can be disengaged from the sleeve or sleeves from outside of the body of the patient, which allows the sleeve(s) to open and the implantable medical device to expand. As discussed above, the implantable medical device can be self-expanding, or the implant can be expanded by a device, such as a balloon.

The coupling member 612 may be, for example, a woven fiber. In other instances, the coupling member 612 can comprise a monofilament fiber. Any type of string, cord, thread, fiber, or wire that is capable of maintaining a sleeve in a tubular shape is within the scope of the present disclosure.

The coupling member 612 or members can be disengaged from the sleeve or sleeves by a mechanical mechanism operated from outside of the body of the patient. For example, the coupling member 612 may be disengaged by applying sufficient tension to the coupling member 612. In another example, a dial or rotational element of a catheter handle can be attached to the coupling member 612 outside of the body. Rotation of the dial or rotational element can provide sufficient tension to, displace and disengage the coupling member 612.

In various embodiments, various components of the devices disclosed herein are steerable. For example, during deployment at a treatment site, one or more of the elongated segments can be configured with a removable steering system that allows an end of the elongated segment to be biased or directed by a user. A removable steering system in accordance with various embodiments can facilitate independent positioning of an elongated segment and can provide for the ability of a user to accomplish any of the types of movements previously described, such as longitudinal movement, rotational movement, lateral movement, or angular movement.

The illustrative components shown in FIGS. 1-6 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIGS. 1-6 may be, in embodiments, integrated with various other components depicted therein (and/or components not illustrated), all of which are considered to be within the ambit of the disclosed subject matter.

It will be apparent to those skilled in the art that various modifications and variations can be made in the present disclosure without departing from the spirit or scope of the disclosure. Thus, it is intended that the present disclosure cover the modifications and variations of this disclosure provided they come within the scope of the appended claims and their equivalents.

Likewise, numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the disclosure, to the full extent indicated by the broad, general meaning of the terms in which the appended claims are expressed. To the extent that these various modifications do not depart from the spirit and scope of the appended claims, they are intended to be encompassed therein.

What is claimed is:

1. An apparatus comprising:
an implantable medical device including a graft portion and a stent portion attached to the graft portion;
a constraining line conduit including a graft material arranged around a circumference of and directly attached to one portion of the implantable medical device forming a lumen formed by a first boundary that includes the graft portion and the stent portion of the implantable medical device and a second boundary that includes the graft material; and
a constraining line arranged through a pathway formed by the lumen of the constraining line conduit without being interwoven with the stent portion and configured to constrain at least another portion of the implantable medical device in response to tensioning of the constraining line.

2. The apparatus of claim 1, wherein the pathway is external of the stent portion.

3. The apparatus of claim 1, wherein the first boundary is formed by an exterior surface of the graft portion of the implantable medical device and the second boundary is formed by the graft material attached to the exterior surface of the graft portion of the implantable medical device.

4. The apparatus of claim 1, wherein the first boundary comprises the graft portion covering the stent portion.

5. The apparatus of claim 1, wherein the constraining line conduit comprises a hollow fiber and the constraining line is arranged within and through the hollow fiber.

6. The apparatus of claim 1, wherein the implantable medical device comprises a deployed configuration and a constrained configuration, and a constrained diameter of the implantable medical device in the constrained configuration is approximately between 5% and 20% of a deployed diameter of the implantable medical device in the deployed configuration.

7. The apparatus of claim 6, wherein the constraining line is configured to adjust the implantable medical device to the constrained configuration in response to the tensioning of the constraining line and to the deployed configuration in response to release of the constraining line.

8. The apparatus of claim 1, wherein the constraining line comprises a loop surrounding a proximal end of the implantable medical device.

9. The apparatus of claim 1, wherein the implantable device includes a constrained configuration and a deployed configuration, the constraining line being configured to partially constrain the implantable device to a partially constrained configuration between the constrained configuration and the deployed configuration.

10. An apparatus comprising:
an implantable medical device including a graft portion and a stent portion attached to the graft portion;
a hollow fiber including an outer circumferential surface at least partially attached to an exterior surface of the implantable medical device and an inner circumferential surface forming a lumen spaced between the implantable medical device formed by an inner circumferential surf ace of the hollow fiber;
a graft material arranged around a circumference of and in contact with one portion of the implantable medical device forming a lumen for the hollow fiber; and
a constraining line arranged through a pathway formed by the lumen of the hollow fiber without being interwoven with the stent portion, the constraining line being configured to constrain at least another portion of the implantable medical device in response to tensioning of the constraining line.

11. The apparatus of claim 10, wherein the graft portion has an interior surface and an exterior surface and the stent portion is attached to the exterior surface of the graft portion.

12. The apparatus of claim 10, wherein the hollow fiber includes a discontinuity or gap to allow for the constraining line to be arranged therein.

13. The apparatus of claim 12, wherein a circumference of the implantable medical device is between 25 mm and 50 mm and the discontinuity or gap in the hollow fiber is between 0.5 mm and 3 mm.

14. The apparatus of claim 10, wherein the implantable medical device comprises a deployed configuration and a constrained configuration, and a constrained diameter of the implantable medical device in the constrained configuration is approximately between 5% and 20% of a deployed diameter of the implantable medical device in the deployed configuration.

15. The apparatus of claim 14, wherein the constraining line comprises a loop surrounding a proximal end of the implantable medical device.

16. The apparatus of claim 14, wherein the constraining line is configured to adjust the implantable medical device to the constrained configuration in response to the tensioning of the constraining line and to the deployed configuration in response to release of the constraining line.

17. The apparatus of claim 10, further comprising a sleeve configured to constrain the implantable medical device in a collapsed configuration.

\* \* \* \* \*